United States Patent [19]

Nagai et al.

[11] Patent Number: 5,306,730

[45] Date of Patent: Apr. 26, 1994

[54] BOTULINUM TOXIN NEUTRALIZER

[75] Inventors: Yoshitaka Nagai, Setagaya; Koutaro Takamizawa, Irima; Ryuichiro Tanaka, Tachikawa; Hiroo Takayama, Tokorozawa; Toshizo Sakurai, Mitaka; Masahiko Mutai, Highashiyamato, all of Japan

[73] Assignee: Kabushiki Kaisha Yakult Honsha, Tokyo, Japan

[21] Appl. No.: 887,652

[22] Filed: May 26, 1992

Related U.S. Application Data

[63] Continuation of Ser. No. 131,237, Dec. 7, 1987, abandoned, which is a continuation-in-part of Ser. No. 11,213, Feb. 3, 1987, abandoned.

[30] Foreign Application Priority Data

Feb. 3, 1986 [JP] Japan .................................. 61-20066

[51] Int. Cl.$^5$ ............................................. A61K 31/20
[52] U.S. Cl. ...................................... 514/558; 514/559; 514/560; 554/1; 554/220; 554/222; 554/224; 554/223
[58] Field of Search .................... 554/1, 220, 222, 224; 514/558, 559, 560, 222, 224

[56] References Cited

U.S. PATENT DOCUMENTS 4,342,789  8/1982  Ueno et al. ........................... 426/266

OTHER PUBLICATIONS

Fugate et al., Applied Microbiology, vol. 21, No. 3, pp. 470-475 (1971).
Blocher et al., Food Technology, vol. 37, No. 11, pp. 87-99 (1983).
Journal of Neurochemistry, vol. 18, (1971), pp. 1751-1759, GB; L. L. Simpson et al.: "The Binding of Botulinum Toxin to membrane lipids: sphingolipids, steroids, and fatty acids".
FEBS, vol. 201, No. 2, (Jun. 1986), pp. 229-232, Federation of European Biochemical Societies; K. Takamizawa et al.: "TLC immunostaining characterization of Clostridium botulinum type A neurotoxin binding to gangliosides and free fatty acids".
Journal of Food Protection, vol. 45, No. 12, Oct. (1982), pp. 1117-1119; M. Dymicky et al.: "Inhibition of Clostridium botulinum 62A by saturated n-aliphatic acids, n-alkyl formates, acetates, propionates and butyrates".

*Primary Examiner*—José G. Dees
*Assistant Examiner*—Porfirio Nazario
*Attorney, Agent, or Firm*—Wenderoth, Lind & Ponack

[57] ABSTRACT

A botulinum toxin neutralizer comprising at least one fatty acid having the number of carbon atoms of at least 12. Such a fatty acid may be any of saturated fatty acids such as lauric acid, myristic acid, palmitic acid, stearic acid, nonadecanoic acid, arachidic acid, and behenic acid or any of unsaturated fatty acids such as oleic acid. The toxin neutralizer acts as if it were an antagonistic receptor for botulinum toxin and, when encountering botulinum toxin in human body, directly combines with the toxin and disables the toxin from combining with the neuromuscular tissues of human body to prevent the outbreak of botulism. The toxin thus neutralized and affixed to the botulinum toxin neutralizer is excreted from the human body. The botulinum toxin neutralizer can be manufactured easily and economically from a naturally occurring glyceride and is thus far less costly then the known antitoxin of ganglioside GT1b produced from bovine brain.

1 Claim, No Drawings

5,306,730

BOTULINUM TOXIN NEUTRALIZER

This application is a continuation of application Ser. No. 07/131,237, filed on Dec. 7, 1987, now abandoned, which is a continuation-in-part of now abandoned application Ser. No. 011,213, filed Feb. 3, 1987.

FIELD OF THE INVENTION

The present invention relates to a botulinum toxin neutralizer which is effective for the prevention and treatment of botulinum intoxication.

BACKGROUND OF THE INVENTION

Botulinum toxin is a proteinous exotoxin secreted by *Clostridium botulinum* broadly distributed in soil and acts at the tips of the motor nerve endings at the neuromuscular junctions. When orally ingested into human body, the botulinum toxin gives rise to intoxication called botulism which is accompanied by paralytic symptoms. The botulism breaks out when the neurotoxin is absorbed from the alimentary tract and combines selectively with the presynaptic membranes at the peripheries of the neuromuscular junctions. The toxin thus interferes with the release of acetylcholine from the chlorinergic motor nerve endings and eventually with conduction of nerve impulses in the terminal branches of the motor nerves to cause neuromuscular relaxing and paralysis characteristic of the botulism. Death may occur from paralysis of respiratory muscles in the worst case.

As to the pathogenic mechanism of the botulinum toxin, it is established that the ganglioside GT1b, an acidic glycolipid present in the presynaptic membrane acts as a receptor for the toxin. While other types of gangliosides such as the gangliosides GQ1b, GD1b and GD1a also have the abilities of combining with botulinum toxin, these gangliosides are less potent than the ganglioside GT1b in combining with botulinum toxin and are, for this reason, considered less responsible for botulism.

The treatment of botulism is extremely difficult and, at the present time, there is practically no other method of treatment than to cease the symptoms once botulism is broken out. In view of the pathogenic mechanism of the botulinum toxin as above discussed, the first conceivable approach to the treatment of botulism may be to use the ganglioside GTbl as an antagonistic receptor for the botulinum toxin since the substance is capable of directly combining with the toxin. For this purpose, the ganglioside GTbl may be orally dosed into human body for direct attachment to the botulinum toxin to prevent the onset of the toxicity thereof. A problem is however encountered in that the source presently available of the ganglioside GTbl is none but the bovine brain, which is so expensive that the method of treating botulism with use of such a ganglioside has seldom been put into practice.

Under these circumstances, it is an object of the present invention to provide an economical botulinum toxin neutralizer which acts as if it were an antagonistic toxin receptor for the treatment of botulism and which will thus facilitate the prevention and treatment of botulism.

SUMMARY OF THE INVENTION

The present invention has been completed through the extensive researches conducted in quest of substances having abilities of neutralizing the botulinum toxin and has resulted from the discovery that there is a family of fatty acids which have potent abilities of combining with and neutralizing the botulinum toxin.

In accordance with an important aspect of the present invention, there is provided a botulinum toxin neutralizer which comprises at least one fatty acid having the number of carbon atoms of at least 12. Preferred examples of such a fatty acid include saturated fatty acids such as, typically, lauric acid with 12 carbon atoms (C12:0), $CH_3(CH_2)_{10}COOH$; myristic acid with 14 carbon atoms (C14:0), $(CH_3(CH_2)_{12}COOH$; palmitic acid 16 carbon atoms (C16:0), $CH_3(CH_2)_{14}COOH$; stearic acid with 18 carbon atoms (C18:0), $CH_3(CH_2)_{16}COOH$; nonadecanoic acid with 19 carbon atoms (C19:0), $CH_3(CH_2)_{17}COOH$; arachidic acid with 20 carbon atoms (C20:0), $CH_3(CH_2)_{18}COOH$; and behenic acid with 22 carbon atoms (C22 0), $CH_3(CH_2)_{20}COOH$, and unsaturated fatty acids such as for example oleic acid with 18 carbon atoms (C18:1), $CH_3(CH_2)_7CH=CH(CH_2)_7COOH$.

In accordance with another outstanding aspect of the present invention, the fatty acid used as a botulinum toxin neutralizer preferably has the number of carbon atoms within the range of 16 to 22, inclusive. Preferred examples of such a fatty acid include saturated fatty acids such as palmitic acid, stearic acid, nonadecanoic acid, arachidic acid, a fatty acid with 21 carbon atoms (C21:0), and behenic acid or unsaturated fatty acids such as oleic acid (C18:1). More preferred of these are palmitic acid and stearic acid for their particularly excellent botulinum toxin neutralizing abilities and the wide availability on a commercial basis of the acids which abundantly occur in various animal and vegetable tissues.

While a botulinum toxin neutralizer according to the present invention may comprise only one of the fatty acids having the number of carbon atoms of 12 or more or preferably within the range of 16 to 22 as above noted, two or more of these may if desired be used in combination to provide a botulinum toxin neutralizer according to the present invention.

The fatty acid which composes a botulinum toxin neutralizer according to the present invention acts as if it were an antagonistic receptor for botulinum toxin and, when encountering botulinum toxin in vivo, directly combines with the toxin and disables the toxin from combining with the neuromuscular tissues of, for example, human body to prevent the outbreak of the botulism. The toxin thus neutralized and affixed to the fatty acid is, as it is, excreted from the human body.

Other important aspects of the present invention will be understood from the following description taken in conjunction with the accompanying drawing. The drawing shows the results of the tests conducted with palmitic acid and ganglioside GT1b using the TLC (thin layer chromatography) immunostaining method to evaluate their abilities to combine with the botulinum type A toxin for comparison between the neutralizing ability of a botulinum toxin neutralizer according to the present invention and that of a known botulinum toxin neutralizing substance.

DETAILED DESCRIPTION OF THE INVENTION

The functions of these higher fatty acids of neutralizing the botulinum toxin have been confirmed by the enzyme-immunostaining and densitometric determination techniques using the known thin layer chromotography (TLC) immunostaining method on thin layer chromatogram plates (H. Higashi et al, J. Biochem. 95, 1517-1520, 1984). Description will be hereinafter made regarding the TLC immunostaining processes thus performed for various fatty acids including those which are operable each or in combination as a botulinum toxin neutralizer according to the present invention.

Prior to these TLC immunostaining processes, sample solutions respectively containing various fatty acids including those having the numbers of carbon atoms of less than 12 and those having the numbers of carbon atoms of 12 or more were prepared. Each of these fatty-acid containing sample solutions was dissolved in a solution of chloroform and methanol mixed in the ratio of 2:1 on a volume basis. The resultant mixture was spotted onto a plastic thin-layer-chromatogram plate (Polygram SilG, manufactured by Marchery-Nagel, West Germany; Mori et al, Biochem. Biophys. Res. Commun. 108, 926-932, 1982), which was then developed with a solution of n-hexane, ether and acetic acid mixed in the ratios of 80:30:1 on a volume basis and was thereafter dried in air. The plate was subsequently dipped in phosphate-buffered saline containing 1% egg albumine, 1% polyvinyl-pyrrolidone and 0.02% sodium azide ($NaN_3$) and was therein incubated at 37° C. for an hour. After the incubation, the plate was washed several times with phosphate-buffered saline containing 3% polyvinylpyrrolidone. An aqueous solution containing the botulinum type A toxin in the concentration of 0.5 microgram/milliliter was applied to the resultant plate in a quantity of 100 microliter/$cm^2$, whereupon the plate was allowed to stand overnight at 4° C. to enable the reaction to proceed. The plate was then washed with phosphate-buffered saline containing 3% polyvinyl-pyrrolidone and was then incubated at 37° C. for two hours with a rabbit antitoxin antiserum applied to the plate. After the incubation, the plate was washed sufficiently with phosphate-buffered saline containing 0.1% Tween 20 (commercially available from Atlas Powder Company) and was then allowed to stand for incubation at 37° C. for 15 minutes in phosphate-buffered saline containing 1% egg albumine, 1% polyvinyl-pyrrolidone and 0.02% sodium azide. The resultant plate was washed with phosphate-buffered saline and was then shaken at 37° C. for 2 hours for reaction in a solution of horseradish-peroxidase (HRP) conjugated anti-rabbit immunoglobulin G (IgG) antibody diluted to 1000-folds with phosphate-buffered saline containing 3% polyvinylpyrrolidone. After the reaction, the plate was washed in phosphate-buffered salt containing 0.1% Tween 20. Fifty mM Tris-chloride buffer solution (pH 7.4) containing 0.01% hydrogen peroxide, 0.05% 4-chloro-1-naphthol and 200 mM sodium chloride was prepared by the method taught by R. Hawkes et al (Anal. Biochem. 119, 142-147, 1982). The buffer solution thus prepared was applied as a substrate to the plate, which was thereafter allowed to stand for 15 minutes at room temperature so that coloring reaction proceeds on the plate. After the coloring reaction, the plate was washed with water and was thereupon dried in air to bring an end to the TLC immunostaining process.

In this TLC immunostaining process, the fatty acid of the sample solution fixed on the chromatogram plate used combines with the botulinum toxin added to the plate if the fatty acid is of the type exhibiting an ability of neutralizing the botulinum toxin. The fatty acid thus combined as a receptor with the botulinum toxin further combines with the rabbit antitoxin antiserum through reaction therewith. When the resultant substance then further reacts with the HRP conjugated anti-rabbit IgG antibody, the antibody combines with the substance antibody or, in effect, the botulinum toxin contained therein. The horseradish peroxidase thus ultimately combined with the botulinum toxin then reacts with the substrate solution containing hydrogen peroxide and 4-chloro-1-naphthol with the result that there occurs decomposition of the substrate or, more precisely, the 4-chloro-1-naphthol component of the substrate solution. The decomposition of the 4-chloro-1-naphthol results in formation of bluish-purple colored spots on the plate. In the case of the sample solution devoid of the botulinum toxin neutralizing ability, the botulinum toxin applied to the chromatogram plate carrying the developed sample solution could not be fixed on the plate and is washed together with the rabbit antitoxin antiserum away before the HRP conjugated anti-rabbit IgG antibody is added to the plate. Accordingly, the HRP conjugated anti-rabbit IgG antibody thereafter added to the plate could not stay on the plate and is therefore also washed away from the plate before the substrate solution is added to the plate. Thus, the substrate solution added to the plate used is allowed to remain chemically intact and will not produce colored spots on the plate.

The areas and concentrations of the bluish-purple colored spots thus produced on the individual chromatogram plates processed with the botulinum toxin-neutralizing fatty acids were determined by densitometric tests using a dual-wave chromatographic scanner (Shimadzu CS-910, manufactured by Shimadzu Seisakusho, Japan) at a wavelength of 570 nanometers. The details of such densitometric determination techniques are described by S. Ando et al, Anal. Biochem. 89, 437-450, 1978. The following table shows the results of the densitometric tests conducted with the sample solutions of various straight-chain saturated fatty acids, wherein the integral values of the peaks observed by the densitometric tests are expressed in terms of index numbers given with the value for the fatty acid (palmitic acid) with 16 carbon atoms used as the base (=100).

| Fatty Acid with Number of Carbon Atoms of: | Integral Value of Densitometric Peaks |
| --- | --- |
| 10 | 5 |
| 12 | 39 |
| 14 | 67 |
| 16 | 100 |
| 18 | 128 |
| 19 | 100 |
| 20 | 89 |
| 21 | 74 |
| 22 | 72 |
| 23 | 68 |
| 24 | 48 |
| 26 | 49 |

From the above table it will be seen that the botulinum toxin neutralizing abilities of fatty acids vary from one of the acids to another depending upon the numbers of the carbon atoms contained in the acids. Thus, it is apparent from the table that fatty acids having the numbers of carbon atoms of 12 or more are particularly efficacious as botulinum toxin neutralizers for their toxin neutralizing abilities represented by the index numbers of more than 30. As noted previously, preferred examples of such fatty acids include saturated fatty acids such as lauric acid with 12 carbon atoms, myristic acid with 14 carbon atoms, palmitic acid with 16 carbon atoms, stearic acid with 18 carbon atoms, nonadecanoic acid with 19 carbon atoms, arachidic acid with 20 carbon atoms and behenic acid with 22 carbon atoms, or unsaturated fatty acids such as oleic acid with 18 carbon atoms (C18:1).

More preferred of these various fatty acids are those having the numbers of carbon atoms within the range of 16 to 22 for their toxin neutralizing abilities represented by the prominently high index numbers indicated in the above table. Such fatty acids include saturated fatty acids such as palmitic acid, stearic acid, nonadecanoic acid, arachidic acid, a fatty acid with 21 carbon atoms (C21:0), and behenic acid or unsaturated fatty acids such as oleic acid. Still more preferred of these are palmitic acid and stearic acid each for their particularly excellent botulinum toxin neutralizing abilities and the wide availability on a commercial basis of the acids which are abundant in animal and vegetable tissues.

Tests have also been conducted on a clinical basis to determine the minimum doses of the botulinum toxin neutralizer according to the present invention as required for the complete neutralization of given quantities of botulinum toxin. These tests have revealed that approximately 50 micrograms of fatty acid with 12 or more carbon atoms is required for the neutralization of 2 micrograms of botulinum toxin. Doses of this order provide a botulinum toxin neutralizing ability approximately equal to one tenth of the antitoxic ability achievable by the botulinum toxin neutralizer of ganglioside GT1b. It is thus considered that a botulinum toxin neutralizer according to the present invention should be used with doses ranging from about 0.5 mg to about 100 mg for the prevention or treatment of botulism.

The following represents certain preferred embodiments of the present invention:

(1) Oral administration of a neutralizer for the treatment of botulinum intoxication For a treatment of a patient actually suffering from botulinum intoxication, a neutralizer constituent is added to a fluid used for an orally administered gastrolavage. An emulsified preparation of the neutralizer containing 15 percent fatty acid and 10–15 percent soybean lecithin (an emulsifying agent) is dispersed in the gastrolavage fluid. The preferable amount of the emulsified preparation added to the fluid ranges from 30 to 40 g (corresponding to 4.5 to 6.0 g of fatty acid) per 300–400 ml of fluid, which amount is generally used for a batch of gastrolavage fluid. Emulsifying agents such as fatty acid glycerin esters or propylene glycol esters can be used in place of soybean lecithin.

After the completion of forced vomiting, a batch of gastrolavage fluid containing the neutralizer, described above, is orally administered to the patient about 20 times in an ordinary manner. The gastrolavage is usually accompanied by intravenous injections of a fluid containing the neutralizer to achieve favorable results, described below.

(2) Intravenous injection for the treatment of botulinum intoxication

A preparation containing a neutralizer is intravenously injected into a patient suffering from botulinum intoxication upon the diagnosis thereof.

The preparation is an emulsion consisting of 10% fatty acid and 15% soybean lecithin in a pyrogen-free sterile saline solution. Emulsifying agents other than soybean lecithin, described above, may also be used.

The injections (10–20 ml) of the neutralizer are given to the patent repeatedly and as many times possible during and after the orally administered gastrolavage treatment, described above.

(3) The neutralizer used as a food additive for the prevention of botulinum intoxication For the prevention of botulinum intoxication, the neutralizer is added to foodstuffs in which *Clostridium botulinum* is likely to grow and produce the botulinum toxin.

An emulsified preparation containing 15% fatty acid and 10–15% soybean lecithin is thoroughly mixed with the food-stuffs, such as fishpaste or minced meats to be processed into canned or bottled foods, sausages or the like. The preferred amount of the emulsified neutralizer added to the foodstuffs ranges from 1 to 5% (preferably 5%) of the weight of the foodstuffs. This preparation can be added, for example in the mincing process of meat used in sausage. As described above, emulsifying agents other than soybean lecithin are also usable.

The neutralizer added to such processed food products is stable and maintains the edibility of the products during storage.

The following is the estimation of the approximate numerical amount of fatty acid necessary to neutralize botulinum toxin:

In vitro tests have revealed that approximately 50 μg of fatty acid with 12 or more carbon atoms is required for the neutralization of 2 μg of botulinum toxin, the amount of toxin deemed to be fatal to humans. As far as the effective treatment or prevention of the botulinum intoxication is concerned, it is theoretically advantageous to use the above-specified fatty acid as much as possible. The amount allowable in the practical use as food additives, however, is limited to a certain value due to the impaired edibility of foodstuffs. Similarly, a limitation is imposed upon the amount allowable in the oral and intravenous administrations due to the impaired safety of patients. Clinical data show that a 100–200 ml dose of a fatty acid emulsion agent containing 10 percent fatty acid, such as linolenic acid, may be used for fluid infusion. According to the estimation based on the above data, intravenous injections of the emulsion, measured 10–20 ml at a time, containing 10 percent neutralizer (corresponding to a dose of 1–3 mg of neutralizer) is believed to be acceptably safe.

Fatty acids with 12 or more carbon atoms are generally stable in chemical nature as well known in the art and can therefore be easily processed into products ready for use as clinical pharmaceuticals or as additives to foods. Such pharmaceuticals may be provided in the forms of tablets, capsulated medicines, sugar-clad drugs, powders and granules, syrups, vialed liquors, suppositories, ointments, intravascular injections and so on.

Tests have further been conducted with palmitic acid and ganglioside GT1b by the TLC immunostaining method to evaluate their abilities to combine with the botulinum type A toxin. The results of these tests are demonstrated in the accompanying drawing. The transverse axis indicates quantities of the sample solutions of palmitic acid and ganglioside GT1b in terms of nano mole while the vertical axis represents the integral values of the peaks observed by the densitometric tests conducted on each of the sample solutions. Thus, the plots shown indicate the relative values representative of the toxin neutralizing abilities of both ganglioside GT1b and palmitic acid when 10 micrograms of each of the toxin neutralizing substance is used as a receptor for botulinum toxin.

It may also be noted that tests have further been conducted by the TLC immunostaining method on such substances as cholesterol, cholesterol esters, triglycerides and phospholipids, none of which has however proved to have a botulinum toxin neutralizing ability.

From the foregoing description it will have been understood that the present invention proposes a useful botulinum toxin neutralizer which is easy to manufacture in various forms. The toxin neutralizer acts as if it were an antagonistic receptor for botulinum toxin and, when brought into contact with botulinum toxin in human body, directly combines with the toxin and disables the toxin from combining with the neuromuscular tissues of human body to prevent botulism. Such a botulinum toxin neutralizer can be manufactured economically from a naturally occurring glyceride and is for this reason far less costly than the antitoxin of ganglioside produced from bovine brain. The fact that a botulinum toxin neutralizer according to the present invention can be manufactured from a naturally occurring substance is important because the substance, which is typically a simple fatty acid, usually provides assurance of pathologic safety to human being. Thus a botulinum toxin neutralizer according to the present invention will contribute significantly to the prevention and treatment of botulism.

What is claimed is:

1. A method of treating a patient suffering from botulinum intoxication which comprises administering to a patient an effective botulinum toxin neutralizing amount of at least one fatty acid having 16 to 22 carbon atoms.

* * * * *